(12) United States Patent
Boyajian et al.

(10) Patent No.: US 10,814,114 B2
(45) Date of Patent: Oct. 27, 2020

(54) METHOD AND APPARATUS FOR APPLYING A TOPICAL SOLUTION

(71) Applicant: DUSA Pharmaceuticals, Inc., Wilmington, MA (US)

(72) Inventors: Thomas Boyajian, Wilmington, MA (US); Mark Carota, Chelmsford, MA (US)

(73) Assignee: DUSA PHARMACEUTICALS, INC., Billerica, MA (US)

( * ) Notice: Subject to any disclaimer, the term of this patent is extended or adjusted under 35 U.S.C. 154(b) by 484 days.

(21) Appl. No.: 15/371,363

(22) Filed: Dec. 7, 2016

(65) Prior Publication Data

US 2017/0157379 A1    Jun. 8, 2017

Related U.S. Application Data

(60) Provisional application No. 62/264,510, filed on Dec. 8, 2015.

(51) Int. Cl.
*A61M 35/00* (2006.01)
*A61J 1/06* (2006.01)
(Continued)

(52) U.S. Cl.
CPC ............ *A61M 35/003* (2013.01); *A61J 1/065* (2013.01); *A61J 1/2089* (2013.01); *A61K 41/0061* (2013.01); *A61N 5/062* (2013.01)

(58) Field of Classification Search
CPC .. A61M 35/003; A61M 35/00; A61M 35/006; A61M 31/00; A61M 37/00; A61K 8/27; A61K 8/29; A61K 8/35; A61K 8/37; A61K 8/40; A61K 8/411; A61K 8/445; A61K 8/466; A61K 8/898; A61K 41/0061; A61K 31/74; A61J 1/065; A61J 1/2089; A61N 5/062; A61H 2201/105; B05C 17/00; B65D 47/42
See application file for complete search history.

(56) References Cited

U.S. PATENT DOCUMENTS 5,954,703 A * 9/1999 Golub ...................... A61K 9/08
604/290
6,991,394 B2 * 1/2006 Tufts ...................... A45D 34/04
401/133

(Continued)

OTHER PUBLICATIONS

Oldani, Peter. "How to use Dermbond Surgical Skin Glue", Inside First Aid, Apr. 13, 2019 (Year: 2019).*

*Primary Examiner* — Tatyana Zalukaeva
*Assistant Examiner* — Gabriella E Burnette
(74) *Attorney, Agent, or Firm* — Foley & Lardner LLP

(57) ABSTRACT

An applicator for dispensing a solution having two or more components includes a hollow body having a head provided at one end of the hollow body for dispersion of the solution and a breaking mechanism attached to the hollow body. The breaking mechanism includes at least one projection extendable into an interior of the hollow body. The applicator further includes a plurality of ampoules placed in the interior of the hollow body. The plurality of ampoules contains the two or more components. Upon activation of the breaking mechanism, the at least one projection applies a force to the plurality of ampoules such that the plurality of ampoules break and release the two or more components to form the solution.

16 Claims, 7 Drawing Sheets

(51) Int. Cl.
    *A61K 41/00*     (2020.01)
    *A61N 5/06*     (2006.01)
    *A61J 1/20*     (2006.01)

(56) References Cited

U.S. PATENT DOCUMENTS

| | | | | |
|---|---|---|---|---|
| 2010/0228193 A1* | 9/2010 | Wyrick | A61M 5/2033 | 604/117 |
| 2011/0137339 A1* | 6/2011 | Stenton | A61B 17/00491 | 606/214 |
| 2015/0306362 A1* | 10/2015 | Battaglia | A61M 35/006 | 206/364 |

* cited by examiner

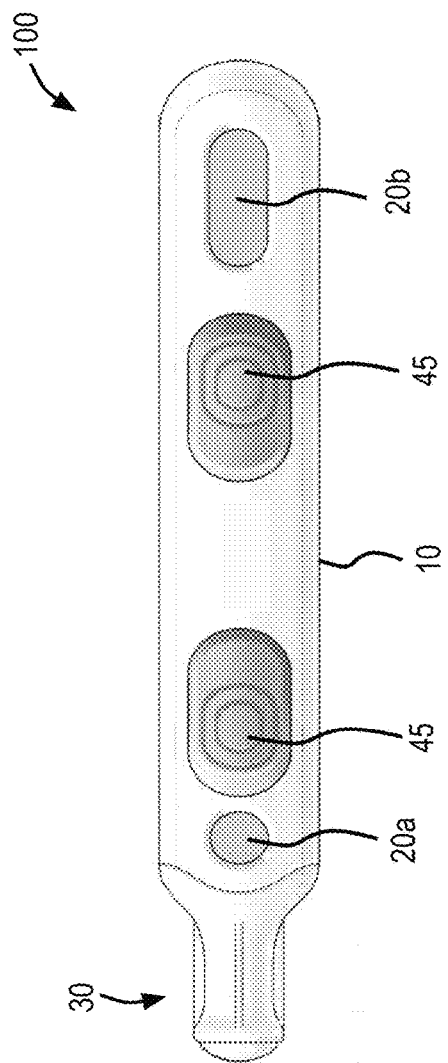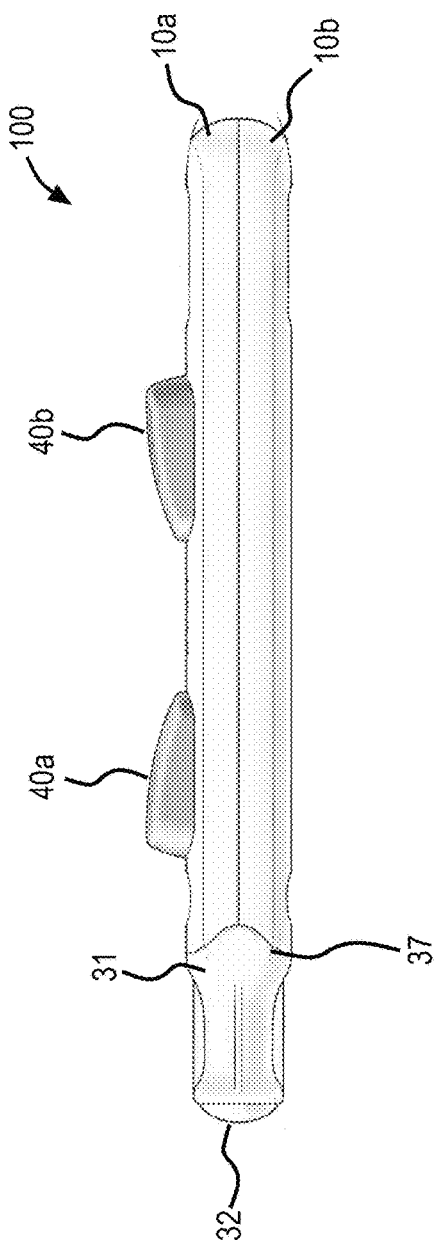

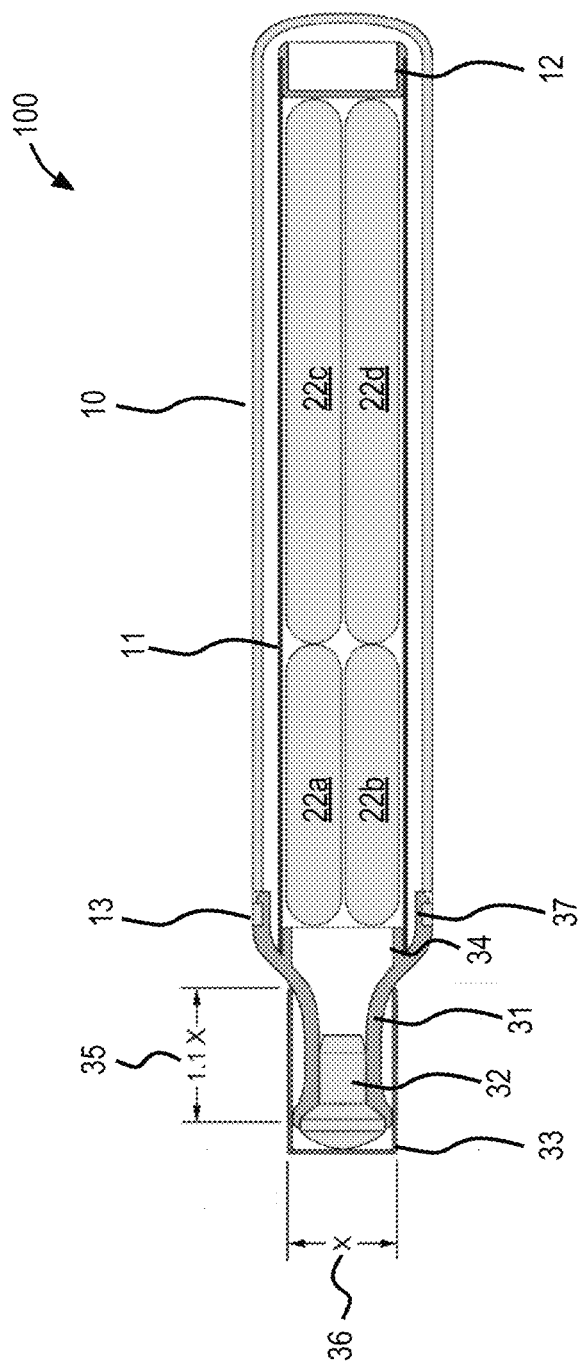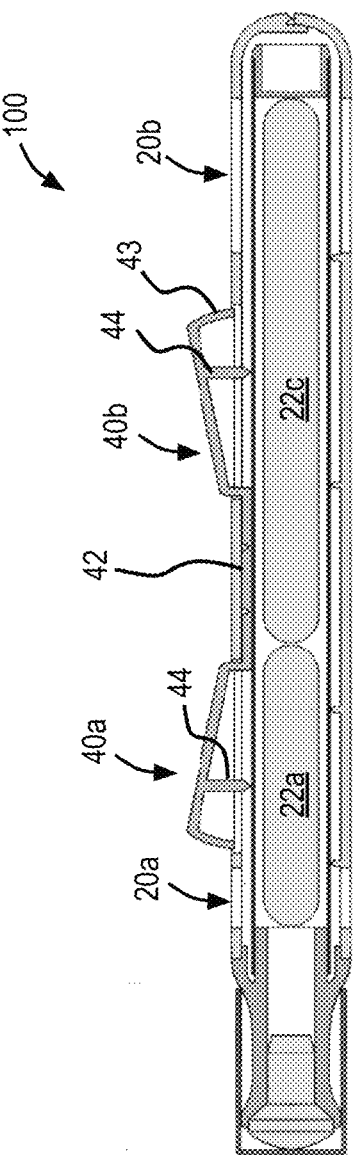

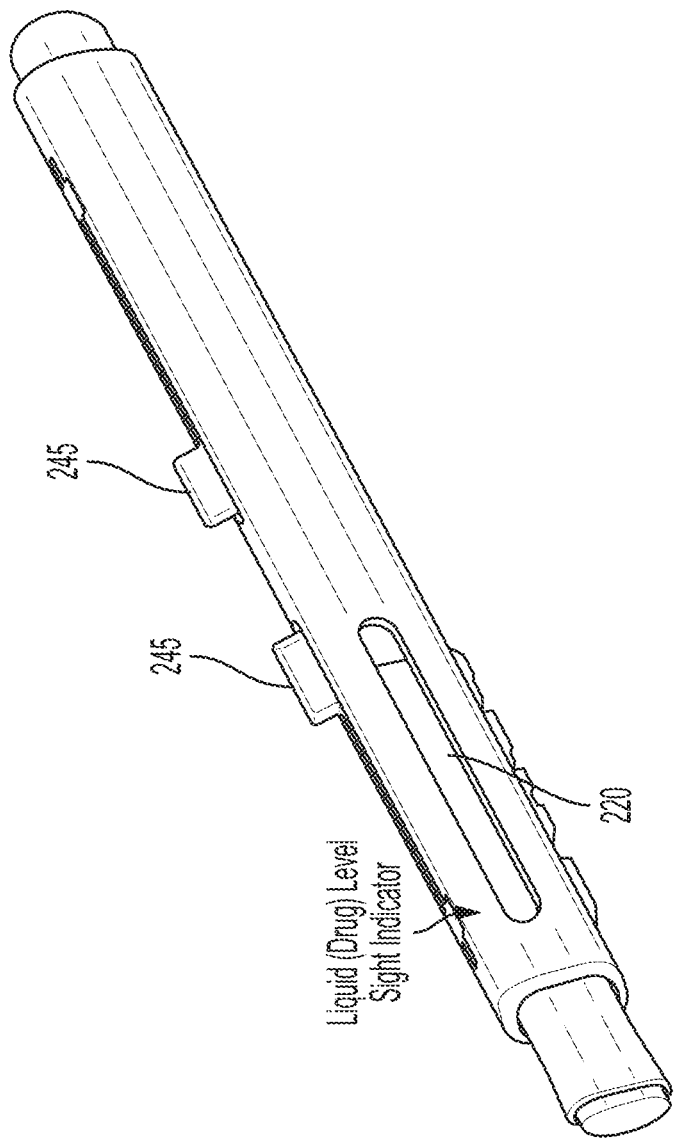

METHOD AND APPARATUS FOR APPLYING A TOPICAL SOLUTION

CROSS-REFERENCE TO RELATED PATENT APPLICATION

The present application claims the benefit of priority to U.S. Provisional Application No. 62/264,510, filed Dec. 8, 2015, the contents of which is hereby incorporated by reference in its entirety.

FIELD

The invention relates generally to an apparatus and method for supplying, mixing, and applying a solution having two or more components for topical use.

BACKGROUND

Photodynamic therapy (PDT), photodynamic diagnosis (PD), or photochemotherapy is generally used to treat and/or diagnose several types of ailments in or near the skin or other tissues, such as those in a body cavity. During one form of PDT or PD, a patient is first administered a photoactivatable agent or a precursor of a photoactivatable agent that accumulates in the tissue to be treated or diagnosed. The area in which the photoactivatable agent is administered is then exposed to visible light, which causes chemical and/or biological changes in the agent. These changes allow the agent to then selectively locate, destroy, or alter the target tissue while, at the same time, causing only mild and reversible damage to other tissues in the treatment area. One example of a precursor of a photoactivatable agent is 5-aminolevulinic acid ("ALA"), which is commonly used in PDT of actinic keratosis.

Typically, ALA is administered as a mixed solution with a liquid diluent and topically applied on a patient's skin just prior to treatment. However, a known complication of ALA is its tendency to degrade when exposed to moisture and/or air. Moreover, degradation of ALA may occur in all sorts of topical vehicles, such as creams, ointments, and solid vehicles. Thus, in order to effectively store ALA until ready for topical application, it is preferable that the agent is stored in a sealed, anhydrous environment.

SUMMARY OF THE INVENTION

One method of storing and administering ALA is through the use of a disposable applicator, such as one disclosed in U.S. Pat. No. 5,954,703, which is incorporated by reference herein in its entirety for the techniques, methods, compositions, and devices related to the application of ALA or other agents for PDT and PD. The applicator includes a hermetically-sealed, essentially frangible compartment enclosed in a deformable container. The frangible compartment may be in the form of a glass ampoule or vial, which holds ALA. Also contained in the deformable container is a liquid diluent to be mixed with the ALA. The liquid diluent may also be contained in a second glass ampoule or vial. When ready to apply the ALA solution, a user squeezes the deformable container such that the ampoule(s) is crushed, allowing the ALA and liquid diluent components to mix. The ALA solution is then controllably applied directly onto a topical surface by a point applicator portion of the container.

In some cases, a large portion of a patient's body is the intended treatment area for PDT and/or PD. In these instances, a large portion of ALA solution must be applied to the patient's body prior to treatment. However, in order to supply a sufficient amount of ALA solution using an applicator such as the one disclosed in U.S. Pat. No. 5,954,703, the applicator must be "sized up," including the glass ampoules, in order to store the proper amount of solution. Such sizing up of the glass ampoules, however, may be relatively difficult to achieve because the walls of the ampoules must remain sufficiently thin to allow for easy breakage. Thus, by increasing the size of the glass ampoules while retaining the thin walls increases the likelihood of structural instability of the ampoules. Moreover, due to pharmaceutical regulatory standards, it may be preferable to retain the size of the ampoules due to established data and safe use of certain sized ampoules. In addition, regulations governing pharmaceutical packaging may further constrain the overall size and basic packaging of the applicator.

In addition, when crushing an applicator such as the one disclosed in U.S. Pat. No. 5,954,703, the user must apply pressure directly to the surface of the container using his hands. This presents the possibility of an uneven application of force to the ampoules, resulting in the possibility that not all of the ampoules are broken. This, in turn, may reduce the likelihood that the components of the solution are properly mixed before application to the intended treatment area.

Therefore, it is an object of some embodiments of the present invention to increase the available volume for storage of the ALA solution components while maintaining a compact structure. It is also an object of some embodiments of the present invention to provide a sufficiently reliable and controlled breaking mechanism for the proper mixing of the ALA solution.

In this regard, one embodiment of the present invention includes an applicator having a plurality of ampoules retained in a compact, hollow body. In addition, the applicator includes one or more breaking mechanisms formed onto the body of the applicator to ensure consistent and reliable breaking of the ampoules for proper mixing of the solution components.

BRIEF DESCRIPTION OF THE DRAWINGS

Features, aspects, and advantages of the present invention will become apparent from the following description and the accompanying exemplary embodiments shown in the drawings, which are briefly described below.

FIGS. 1A-1C show top, side, and bottom views of an applicator according to an exemplary embodiment.

FIGS. 3A-3B show schematic bottom and side views of an interior of the applicator of FIGS. 1A-1C.

FIGS. 4A-4B show perspective views of an applicator according to another exemplary embodiment.

DETAILED DESCRIPTION

Figure 1C:
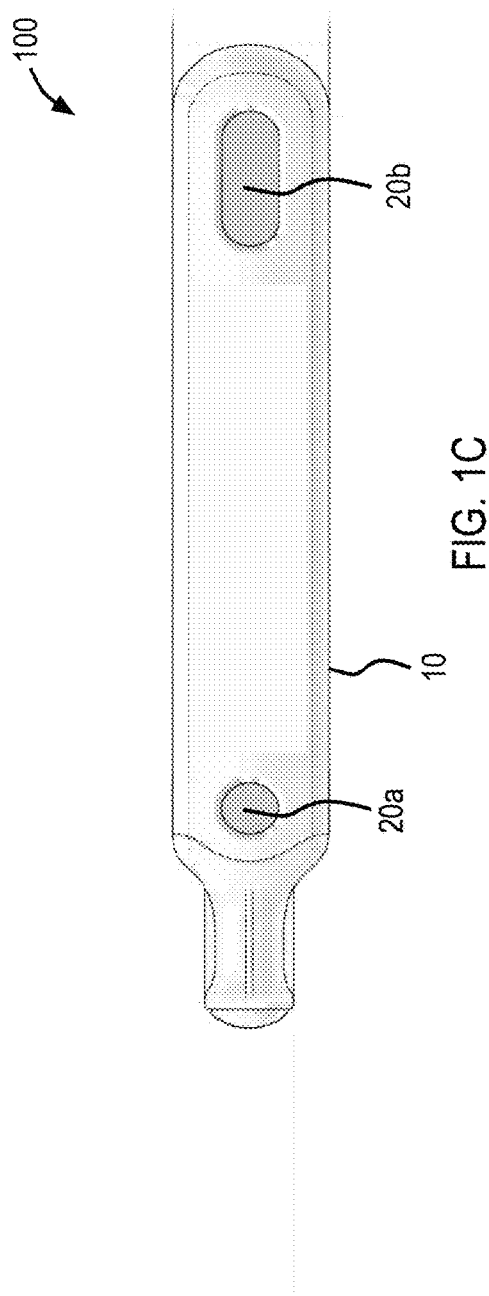

FIGS. 1A-1C illustrate one embodiment of an applicator according to the present invention. As shown in FIGS. 1A-1C, the applicator 100 is formed as a tertiary structure having a case 10, which includes two separate parts 10a and 10b fitted together along a midline, and an applicator head 30 attached to one end of the case 10. The case 10 may be generally oblong in shape, but may be any other appropriate shape, while the applicator head 30 tapers from the case 10 and narrows to form a ball-point tip or other type of applicator tip. The case 10 and the applicator head 30 may be made of any suitable material. Preferably, the case 10 and the applicator head 30 are made of a rigid plastic material, such as polyvinyl chloride (PVC).

Figure 2:
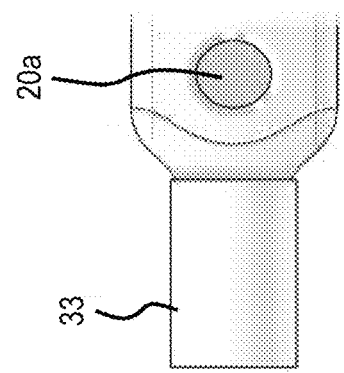
FIG. 2 shows a detailed view of an applicator head of the applicator of FIGS. 1A-1C.

The applicator head 30 further includes a frame 31 and an applicator pad 32 attached to one end of the frame 31. As shown in FIG. 3A, at an opposite end of the frame 31, the frame 31 includes a recessed portion 37, which is formed to receive a protrusion 13 formed at an open end of the case 10, allowing the applicator head 30 to be snap-fitted onto the case 10 and resulting in a closed hollow body to hold the solution components. As shown in FIG. 3A, the frame 31 preferably has a length 35 to width 36 ratio of about 1.1 to 1 to allow for increased usability and comfort. As further shown in FIGS. 3A-3B, the applicator pad 32 partially extends into the frame 31, which bows inwardly toward its end such that the applicator pad 32 is held in the frame 31 by a form fit. The applicator pad 32 is preferably made from an absorbent material (e.g., cotton, nylon, or a sintered plastic copolymer) such that the distribution and application of the topical solution contained within the applicator 100 may be controlled. The applicator head 30 may also include a cap 33, shown in greater detail in FIG. 2. The cap 33 serves to cover the applicator pad 32, which ensures proper sterilization of the applicator 100 and its interior components and maintains the sealed, anhydrous environment.

The interior of the applicator 100 includes a plurality of ampoules 22a-22d encased in a sheath 11. In the exemplary embodiment shown in FIGS. 3A-3B, the plurality of ampoules 22a-22d consists of four ampoules. However, the plurality of ampoules is not necessarily limited to four ampoules and may consist of any number of ampoules, such as two, three, five, or six, or more ampoules. The sheath 11 is preferably made of a deformable material that is resistant to puncture and/or scoring. For example, the sheath 11 may be made of a plastic material, such as polyethylene (e.g., low-density polyethylene or high density polyethylene), polypropylene, butyrate, propylene copolymers, and other equivalent materials. Attached to one end of the sheath 11 is a rigid end part 12, which holds the sheath 11 within the case 10. The opposite end of the sheath 11 is then attached to an attachment flange 34 of the applicator head 30. This creates a sealed environment closed to moisture and/or air for the ampoules 22a-22d. In addition, the sheath 11 serves as a container in which the solution components may be mixed and held during application.

Placed within the sheath 11 are the four ampoules 22a-22d. The ampoules 22a-22d may be formed of a glass material, such as borosilicate, and may be formed to have thin, onion skin-like walls for easy breakage. In the embodiment shown in FIGS. 3A-3B, two of the ampoules 22a, 22b are made smaller than the other two ampoules 22c, 22d. Alternatively, however, the ampoules 22a-22d may be of equal size or each of different sizes. In general, the ampoules 22a-22d are sized such that each contain the proper amount of components to ensure the correct potency and volume of the solution to be applied.

As shown in FIGS. 3A-3B, the smaller of the two ampoules 22a, 22b are provided proximate to the applicator head 30, while the larger of the two ampoules 22c, 22d are provided distal to the applicator head 30. The ampoules 22a, 22b may each be configured with a volume that can hold an amount ranging from about 0.17 mg to about 0.52 mg of anhydrous ALA or other component in powder form. In particular embodiments, the ampoules 22a, 22b are each configured to hold an amount of about 0.345 mg of anhydrous ALA or other component in powder form. In addition, ampoules 22c, 22d may each be configured to hold a volume, for example, ranging from about 0.75 ml to about 2.25 ml of a liquid diluent. In particular embodiments, ampoules 22c, 22d are each configured to hold a volume of about 1.5 ml of a liquid diluent. With the use of four ampoules, the amount of solution that the applicator 100 can hold may be increased. At the same time, the compact shape of the applicator 100 and the thin walls of the ampoules 22a-22d may also be retained in order to maintain ease of breakage and greater constituent volume. In some embodiments, the applicator 100 may be capable of dispensing up to a total volume ranging from about 1.5 ml to about 4.5 ml of a topical solution.

In certain embodiments, the applicator 100 may be capable of dispensing up to a total volume of about 3 ml of a topical solution.

In one embodiment, the ampoules 22a, 22b contain essentially anhydrous ALA, while the ampoules 22c, 22d contain a liquid diluent or, more generally, a topical solution vehicle (TSV). Once the ampoules 22a-22d have been filled with the appropriate material, the ampoules 22a-22d may be topped with nitrogen, an inert gas, or evacuated before being hermetically sealed. Hermetic sealing of the ampoules 22a-22d prevents exposing the essentially anhydrous ALA to moisture and/or air and allows the solution components to remain separate until ready for application. In addition, due to maintaining a relatively small size with regard to the individual ampoules, smaller head spaces in each of the ampoules may be achieved, enhancing stability and allowing less contact with non-formulation elements (e.g., air and other gases that may be trapped in a given ampoule).

The liquid diluent or TSV may be any suitable diluent or solution that permits mixing with the essentially anhydrous ALA. One preferable liquid diluent that may be used is an alcohol and water solution. The solution may also include a wetting agent and/or a humectant. A range of weight/weight percentages for a preferred solution are 39.9-48.8 Alcohol (USP or SDA 40-2), 39.1-47.8 Purified Water USP, 5.9-7.4 LAURETH-4, 3.5-4.3 Isopropyl Alcohol USP, and 1.5-1.8 Polyethylene Glycol 400 NF. The weight/weight percentages of a particularly preferred diluent are 44.37 Alcohol (USP or SDA 40-2), 43.46 Purified Water USP, 6.59 LAURETH-4, 3.93 Isopropyl Alcohol USP, and 1.65 Polyethylene Glycol 400 NF. However, the composition of the liquid diluent or TSV is not particularly limited. For example, various other alcohol/water percentages may be used, various surfactants may be substituted for the LAURETH-4 (e.g., sodium lauryl sulfate, as well as other ionic or nonionic surfactants), and propylene glycol or glycerin may be substituted for the polyethylene glycol.

In order to break the ampoules 22a-22d to release its components, the applicator 100 is provided with a breaking mechanism in the form of two buttons 40a, 40b attached to the case 10, as shown in FIGS. 1A-1B. As further illustrated in FIG. 3B, a connection portion 42 connects the buttons 40a, 40b to one another and further connects the buttons 40a, 40b to the case 10. The buttons 40a, 40b generally include a sloped upper face and an outer flange 43 that serves to guide the movement of the buttons 40a, 40b within the case 10 as the buttons 40a, 40b are depressed. As shown in FIG. 1A, the sloped upper face of the buttons 40a, 40b may include grooves and/or depressions 45 that are configured to allow a user's finger to comfortably rest on the buttons 40a, 40b when in use.

As shown in FIG. 3B, formed within an inner portion of the buttons 40a, 40b is a projection 44. The tip of the projection 44 spans across at least two of the ampoules (e.g., ampoules 22a, 22b) such that when a button (e.g., button 40a) is depressed, the projection 44 applies an even and constant force to the ampoules. This even application of force allows both ampoules to break simultaneously and reliably when the button is pushed by the user. Alternatively, each button (e.g., button 40a) may be provided with two projections 44, each of which crushes one ampoule (e.g., ampoule 22a). In addition, only one button may be provided, which may be configured to depress one or more projections that break all four ampoules 22a-22d simultaneously. For example, one button may be configured to depress connection portion 42, which allows projections 44 to simultaneously break and/or crush the ampoules 22a-22d.

The buttons 40a, 40b and the connection portion 42 are preferably made of a bendable, yet rigid plastic material. Thus, when a user depresses a button (e.g., button 40a) in order to break and/or crush the ampoules (e.g., 22a, 22b) contained in the sheath 11, the button 40a rotates about a pivot point at its connection to the connection portion 42 as the outer flange 43 guides the movement of the button 40a within the case 10. As the button 40a rotates, the projection 44 moves downward to press against the sheath 11 and the ampoules 22a, 22b. When pressed, the sheath 11 deforms inwardly, but is not punctured by the projection 44 and instead remains intact. The ampoules 22a, 22b, however, are simultaneously crushed by the force applied by the projection 44 and its contents are then released into the sheath 11. Once all ampoules 22a-22d have been crushed and their contents mixed, the topical solution may then flow through the applicator pad 32 to be applied to a treatment area. In addition, the applicator pad 32 may serve as a filter to prevent the crushed ampoules 22a-22d from exiting the applicator 100 during application. Moreover, in some embodiments, the buttons 40a, 40b and the case 10 are sufficiently rigid to prevent unintentional breakage of the ampoules 22a-22d. For example, the buttons 40a, 40b may be configured so as to require a sufficient force to crush the ampoules 22a-22d such that unintentional depression of the buttons 40a, 40b will prevent breakage of the ampoules 22a-22d. Alternatively, in other embodiments, the buttons 40a, 40b may include a lock or other safety feature to prevent unintentional depression of the buttons 40a, 40b. For example, the lock may be a removable tamper-proof safety feature that a user may remove from the applicator 100 when needed for a first time use. In addition, the lock may be a permanent safety feature that a user may activate or deactivate (e.g., slide into activated or deactivated positions) to lock or unlock the buttons 40a, 40b during multiple uses of the applicator 100.

As shown in FIGS. 1A and 1C, the applicator 100 may further include two indicators 20a and 20b. The indicators 20a, 20b are formed as apertures located on both the top and bottom parts 10a, 10b of the case 10. In addition, the indicators 20a, 20b formed on the top part 10a may be aligned with the indicators 20a, 20b formed on the bottom part 10b such that the user can look directly through the interior of the case 10 when held up to a light. The indicators 20a, 20b may also include a transparent material, such as a clear plastic, so as to cover the sheath 11, or the indicators 20a, 20b may simply be holes formed within the case 10. The sheath 11 is also made transparent to allow the user to view the solution contained within the sheath 11.

The indicators 20a, 20b may serve to indicate the level of solution remaining in the applicator 100 during use. In addition, the indicators 20a, 20b may also allow the user to confirm that the ampoules have been properly crushed and/or confirm that the solution has been sufficiently mixed. In the applicator 100 shown in FIGS. 1A and 1B, indicator 20a is formed as a circular aperture, while indicator 20b is formed as a larger, oval aperture. In this regard, indicator 20a may serve to indicate to the user the level of solution remaining in the applicator 100 during application of the solution to a patient (i.e., when the applicator 100 is tilted up in order to allow the solution to flow through the applicator pad 32). On the other hand, indicator 20b may serve to indicate proper mixing of the solution when the ampoules have been crushed and before application of the solution, as the applicator 100 is being held upright by the user. However, the shape of the indicators 20a, 20b is not particularly limited, nor is the number of indicators that may be formed on the case 10.

The components contained in the ampoules 22a-22d are also not particularly limited. Thus, applicator 100 may be configured to store two or more incompatible materials that may be later mixed when needed. In addition, the applicator 100 may be configured to hold thermogenic solutions, which may allow for faster absorption and/or drying when applied to the treatment area. Furthermore, the applicator 100 may be configured to heat the solution before application of the treatment area. This may be preferable when handling solutions that need to be activated by the application of heat before use or when lending heat to the solution allows for faster absorption and/or drying. In this configuration, the case 10 further includes a heating wire, in the form of, for example, a copper wire, mounted in the interior of the case 10, but outside of the sheath 11. The copper wire may be inductively heated in order to heat the formulation after mixing of the components. When using an ALA solution with the applicator 100, copper may affect the stability of the ALA solution and cause the essentially anhydrous ALA to degrade. Thus, by placing the copper wire between the sheath 11 and the case 10, the ALA solution may be isolated from the copper while still having the benefit of being heated before application for increased absorption and/or drying.

According to one method of applying an ALA solution to an intended treatment area using the applicator 100, a user first depresses the button 40b of the applicator 100 to simultaneously break the ampoules 22c, 22d, releasing the liquid diluent into the sheath 11. Next, the user depresses the button 40a to simultaneously break the ampoules 22a, 22b in order to release the essentially anhydrous ALA into the sheath. The user then gently shakes the applicator 100 to mix the essentially anhydrous ALA with the liquid diluent. Alternatively, the user may depress the button 40a first or may depress both buttons 40a, 40b at the same time when mixing the solution.

Once the ampoules have been broken and the contents sufficiently mixed, which may be confirmed by the user using the indicator 20b as described above, the applicator 100 is tilted so that the ALA solution flows toward the applicator pad 32. Application of the solution is accomplished by pressing and releasing the applicator pad 32 against the area to be treated. In some embodiments, only the intended treatment area (e.g., a lesion), and not the surrounding skin, is uniformly wetted and then allowed to dry. After the original application has dried, the treatment may be repeated for multiple applications, preferably for a total of two applications. Preferably, the topical surface is an external surface of a patient, such as the skin. However, internal surfaces, such as vaginal, rectal, or oral surfaces, may also be treated according to the present invention.

Figure 4A:
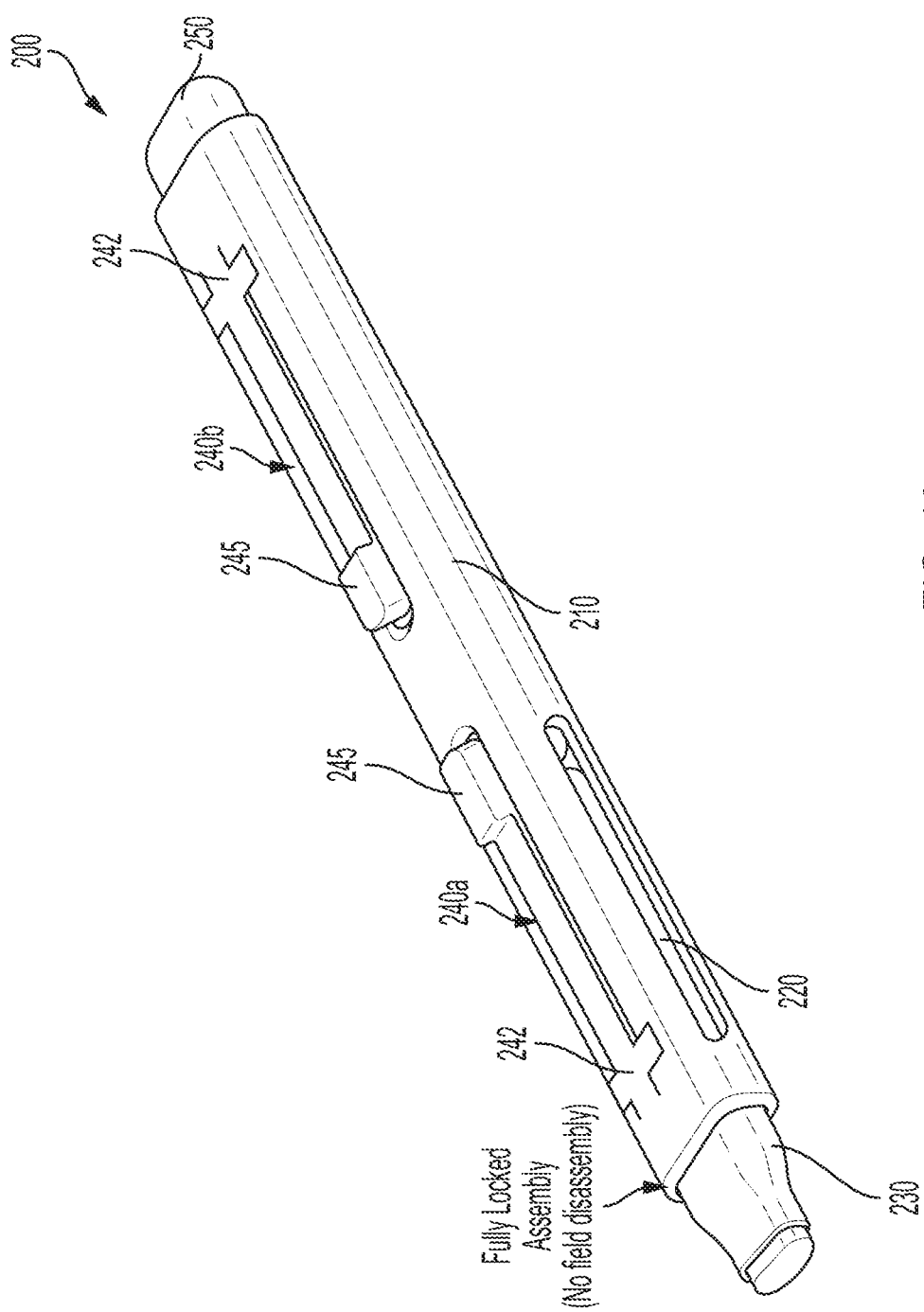
Figure 5:
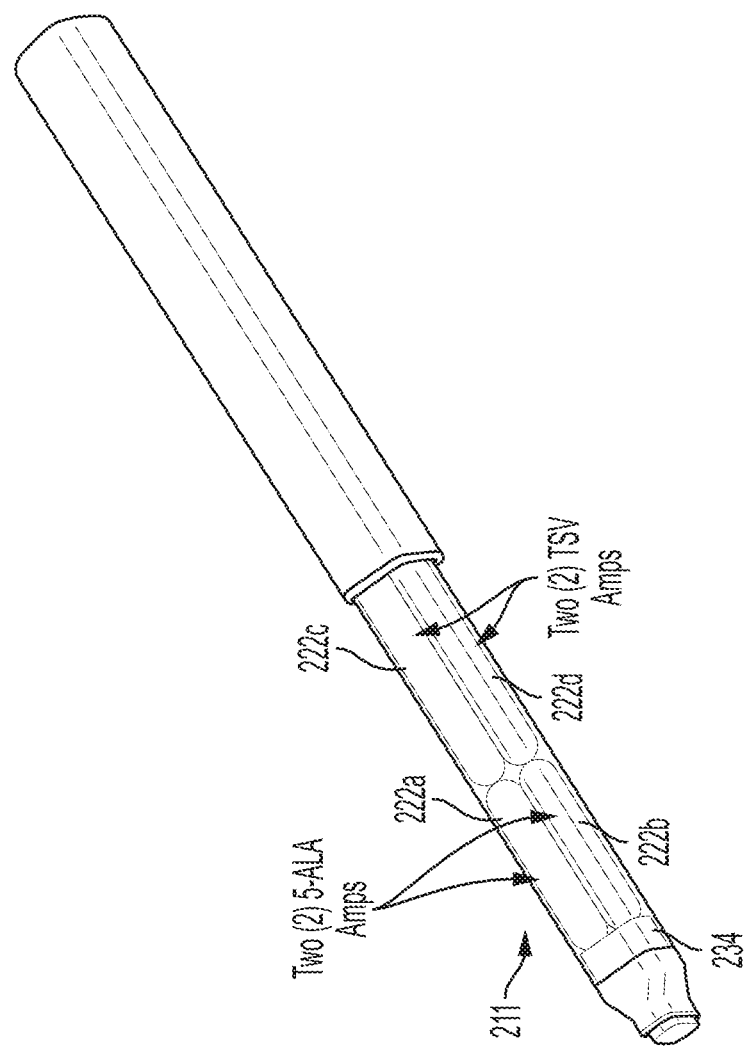
FIG. 5 shows a perspective view of the applicator of FIGS. 4A-4B with its case partially removed to illustrate interior components.

FIGS. 4A-4B and 5 show a second embodiment of an applicator 200. In this embodiment, the buttons 240a, 240b are integrally formed in the case 210. The buttons 240a, 240b pivotally connect to the case 210 at connection portions 242. When a user depresses the buttons 240a, 240b by pressing down on a pressing knob 245, the buttons 240a, 240b pivot downwardly about the connection portions 242 to press against and deform the sheath 211 and subsequently crush the ampoules 222a-222d (shown in FIG. 5) inside the case 210. As shown in FIG. 4B, the applicator 200 includes an indicator 220, which can be formed of a transparent material or simply be a hole formed within the case 210, placed on a side of the case 210 for viewing of the interior components of the applicator 200.

In addition, as illustrated in FIGS. 4A-4B, the applicator 200 may further include a skin preparation element 250 attached to the case 210 at an end opposite to that of the applicator head 230. The skin preparation element 250 may be used in conjunction with the solution to be applied for treatment. For example, the skin preparation element 250 may take the form of microneedles that can be used to scrape or puncture the skin prior to application of the solution, such that absorption of the solution may be enhanced when applied.

Figure 6A:
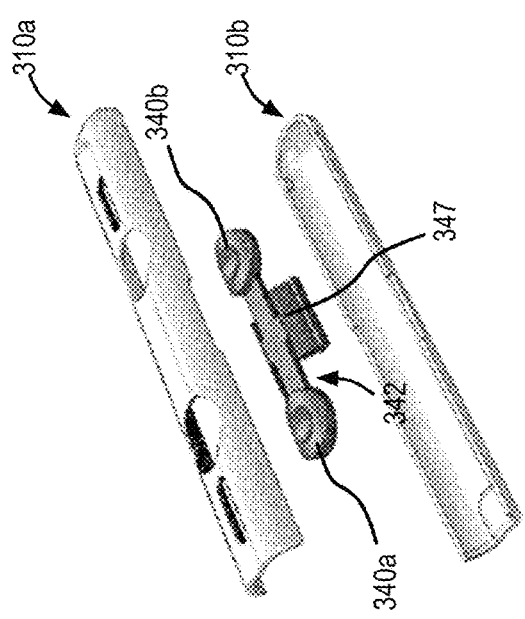
FIGS. 6A-6B show perspective views of an applicator according to yet another exemplary embodiment.
Figure 6B:
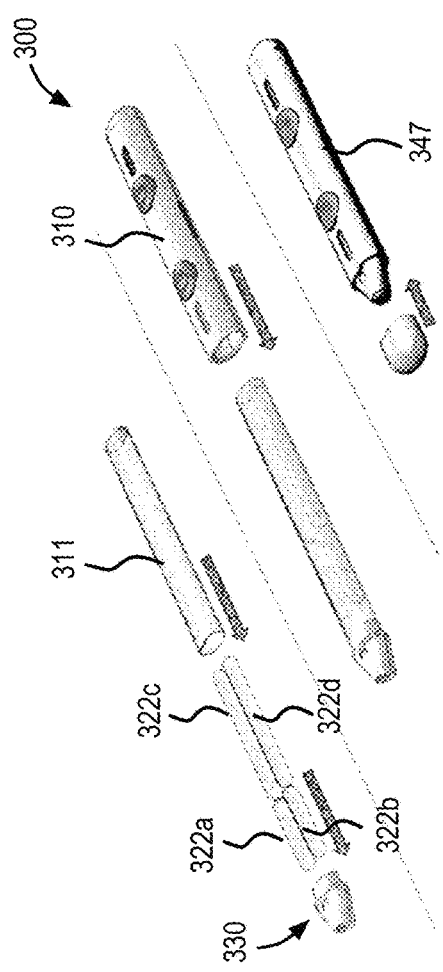

FIGS. 6A-6B show a third embodiment of an applicator 300. The applicator 300 is also formed as a tertiary structure and includes a case 310 having two parts 310a and 310b fitted together at a midline, and an applicator head 330 attached to one end of the case 310. A breaking mechanism in the form of two buttons 340a, 340b connected together by a connecting portion 342 attaches to the case 310. The connecting portion 342 includes lower extending flanges 347, which allow for attachment to the case 310 by a snap-fit. Similar to the applicator 100 of the first embodiment, the applicator 300 further includes a sheath 311, which holds four ampoules 322a-322d, attached to the applicator head 330.

As described above, the applicator of the present invention allows for a compact system, which is capable of providing an increased amount of solution for the application of larger treatment areas. In addition, the applicator of the present invention allows for a more reliable method of storing and then mixing incompatible materials until just prior to application, ensuring greater stability while the components are being stored and greater consistency when the components are subsequently mixed. Additional advantages and modifications will readily occur to those skilled in the art. Therefore, the invention is not limited to the specific details and representative devices, shown and described herein. Accordingly, various modifications may be made without departing from the spirit and scope of the general inventive concept as defined by the appended claims and their equivalents.

What is claimed is:

1. An applicator for dispensing a solution having two or more components, comprising:
    a hollow body having a head provided at one end of the hollow body for dispersion of the solution;
    a first breaking mechanism attached to the hollow body, wherein the first breaking mechanism includes at least one first projection extendible into an interior of the hollow body;
    a second breaking mechanism attached to the hollow body, wherein the second breaking mechanism includes at least one second projection extendible into the interior of the hollow body;
    a first plurality of ampoules placed in the interior of the hollow body, wherein the first plurality of ampoules contains the two or more components, and
    a second plurality of ampoules placed in the interior of the hollow body, wherein the second plurality of ampoules contains the two or more components, the second plurality of ampoules being adjacent and parallel to the first plurality of ampoules,
    wherein, upon activation of the first breaking mechanism and the second breaking mechanism, the at least one first projection and the at least one second projection apply force to the first plurality of ampoules and the second plurality of ampoules such that the first plurality of ampoules and the second plurality of ampoules break and release the two or more components to form the solution in the hollow body,
    wherein the first breaking mechanism and the second breaking mechanism collectively include two buttons, wherein each of the buttons includes a projection extendible into the interior of the hollow body, and
    wherein the first plurality of ampoules comprises ampoules differing in contents from each other, and the second plurality of ampoules comprises ampoules differing in contents from each other.

2. The applicator of claim 1, wherein at least one of the first plurality of ampoules contains 5-aminolevulinic acid.

3. The applicator of claim 1, wherein at least one of the first plurality of ampoules contains a liquid diluent for 5-aminolevulinic acid.

4. The applicator of claim 3, wherein the liquid diluent is an alcohol and water solution.

5. The applicator of claim 1, wherein at least one of the first plurality of ampoules is configured to hold an amount ranging from about 0.17 to 0.52 mg of a component.

6. The applicator of claim 5, wherein an other at least one of the first plurality of ampoules is configured to hold an amount ranging from about 0.75 to 2.25 ml of a component.

7. The applicator of claim 6, wherein at least one of the second plurality of ampoules contains 5-aminolevulinic acid.

8. The applicator of claim 7, wherein at least one of the second plurality of ampoules contains a liquid diluent for 5-aminolevulinic acid.

9. The applicator of claim 1, wherein a first button of the two buttons is configured to simultaneously break one ampoule of the first plurality of ampoules and another ampoule of the second plurality of ampoules.

10. The applicator of claim 9, wherein an other of the two buttons is configured to simultaneously break an other at least two ampoules of the first and second pluralities of ampoules.

11. The applicator of claim 1, wherein each of the first plurality of ampoules contains a different component.

12. The applicator of claim 1, wherein the solution comprises a thermogenic solution.

13. The applicator of claim 1, wherein the hollow body further includes a skin preparation element provided at an other end of the hollow body.

14. The applicator of claim 1, wherein the first plurality of ampoules is provided in a sheath, and wherein the sheath is provided in the interior of the hollow body.

15. The applicator of claim 1, wherein the hollow body further includes an indicator configured to indicate an amount of solution remaining in the applicator.

16. The applicator of claim 1, wherein the first plurality of ampoules and the second plurality of ampoules comprise four ampoules.

* * * * *